(12) United States Patent
Welter et al.

(10) Patent No.: US 6,455,241 B1
(45) Date of Patent: Sep. 24, 2002

(54) PHOTOGRAPHIC ELEMENT CONTAINING IMIDAZOLONOYLACENTANILIDE COUPLER

(75) Inventors: Thomas R. Welter, Webster; Frank D. Coms, Fairport, both of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/844,458

(22) Filed: Apr. 27, 2001

(51) Int. Cl.⁷ .............................. G03C 1/08; G03C 7/26; G03C 7/32
(52) U.S. Cl. ........................................ 430/557; 430/556
(58) Field of Search ................. 430/543, 557, 430/556

(56) References Cited

U.S. PATENT DOCUMENTS

| | | | | |
|---|---|---|---|---|
| 5,674,667 A | * | 10/1997 | Clark et al. | 430/388 |
| 6,015,658 A | * | 1/2000 | Welter et al. | 430/557 |
| 6,057,087 A | | 5/2000 | Welter et al. | |
| 6,083,677 A | | 7/2000 | Welter et al. | |
| 6,221,573 B1 | * | 4/2001 | Abu-Hasanayn et al. | 430/556 |

* cited by examiner

*Primary Examiner*—Geraldine Letscher
(74) *Attorney, Agent, or Firm*—Aurthur E. Kluegel

(57) ABSTRACT

Disclosed is a photographic element comprising a light sensitive silver halide emulsion layer having associated therewith a coupler represented by formula F-1,

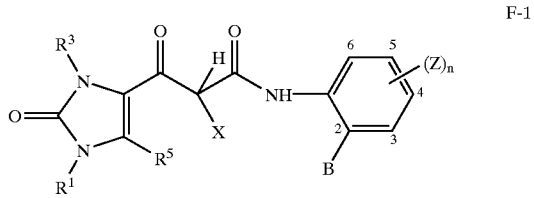

wherein:

$R^1$, $R^3$ and $R^5$ are independently selected from hydrogen or a substituent group and two of them may join to form a ring;

X is hydrogen or a coupling-off group,

B is hydrogen or a substituent group;

Z is a substituent group, and n varies from 0–4.

The element exhibits improved dye-forming activity and an improved combination of dye hue and dye stability.

14 Claims, No Drawings

PHOTOGRAPHIC ELEMENT CONTAINING IMIDAZOLONOYLACENTANILIDE COUPLER

FIELD OF THE INVENTION

The invention relates to a photographic element comprising a light sensitive silver halide emulsion layer having associated therewith a certain imidazolonoylacetanilide type coupler having improved coupling activity and that forms a yellow dye that exhibits an improved combination of hue and stability.

BACKGROUND OF THE INVENTION

Conventional color photographic images are formed via a chromogenic development process. After exposure of a color photographic element, the object scene is stored as a composite of red, green and blue silver halide latent images. During the color development process, these silver halide latent images are reductively developed, an oxidation product of this development reacts with cyan, magenta or yellow dye-forming couplers. The composite dye image is then formed by the superpositioning of the cyan, magenta and yellow dye images to afford a reproduction of the original scene. The controlled conversion of silver halide latent image to color dye image is the goal of color photographic chemistry. The yield of dye color density from each unit of silver halide developed is a measure of coupler activity. Clearly, the higher the activity of a coupler the less silver halide is needed to allow effective image formation. The reduction in the amount of silver halide used in a photographic systems can lead to improved photographic image reproduction, lower cost photographic products, and less potential environmental concerns from development processes. Coupler or dye-forming activity, as defined herein, is composed of two prime factors: (1) the efficiency of the dye formation process, i.e., the chemistry converting coupler to dye, and (2) the light absorption properties of the chromogenically formed dye, i.e., the dye's spectral bandshape and extinction. Improvements in dye extinction are realized as improvements in coupler activity and may thereby lead to silver halide reductions.

Two further important features of photographic reproductions are their color fidelity and their image stabilities. To efficiently reproduce a wide gamut of hues, the dyes comprising the color image must exhibit relatively sharp cutting spectral curves. Additionally, the dye's spectral response curve must be carefully placed, i.e., have a well-positioned maximum absorption, to afford the desired color reproduction.

Color photographic images slowly degrade when stored under ambient conditions. Dyes, especially yellow dyes, of pictures held in the dark, that is, stored in albums, boxes or slide trays and not exposed to direct light, degrade primarily via hydrolytic mechanisms. These image dyes, when exposed to light, fade both via the hydrolytic mechanisms as well as via photochemical processes. The stability of a color image is clearly dependent upon the stabilities of its component dyes. It is apparent from these considerations that the hydrolytic stability of photographic dyes is of primary importance to image stability. The destruction of photographic dyes may be catalyzed by either acids or bases; dyes that are robustly stable to various hydrolytic conditions will provide more stable photographic images. The importance of the stability of azomethine yellow dyes toward acid catalyzed hydrolysis has been noted.

New classes of photographic yellow couplers were recently disclosed by Welter and Reynolds in U.S. Pat. Nos. 6,057,087 and 6,083,677. These patents describe new classes of azoloylacetanilide photographic couplers that provide dyes with improved spectral characteristics and stabilities. Conventional yellow dye-forming couplers include the common pivaloylacetanilide coupler class and related dyes.

It has now been found that certain new imidazolonoylacetanilide type yellow couplers can afford yellow azomethine dyes with high coupling activity, improved hues and enhanced hydrolytic stabilities over that provided by acylacetanilide couplers known heretofore.

SUMMARY OF THE INVENTION

The invention provides a photographic element comprising a light sensitive silver halide emulsion layer having associated therewith a coupler represented by formula F-1,

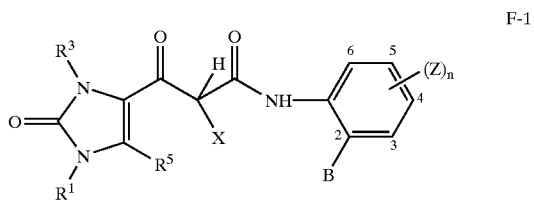

wherein:
  $R^1$, $R^3$ and $R^5$ are independently selected from hydrogen or a substituent group and two of them may join to form a ring;
  X is hydrogen or a coupling-off group;
  B is hydrogen or a substituent group;
  Z is a substituent group, and n varies from 0–4.

The element exhibits improved dye-forming activity and an improved combination of dye hue and dye stability.

DETAILED DESCRIPTION OF THE INVENTION

The invention is generally as described above for formula F-1. $R^1$, $R^3$ and $R^5$ are independently selected from hydrogen or a substituent group and two of them may join to form a ring. Typically, $R^1$ is a (cyclo)alkyl, aryl or heterocyclic group such as an alkyl e.g. a methyl, butyl, octyl, dodecyl, benzyl, or a phenyl group. $R^3$ and $R^5$ are typically independently selected hydrogen or (cyclo)alkyl, aryl or heterocyclic groups such as an alkyl group e.g. a methyl, octyl group, aryl, e.g. naphthyl, or phenyl group, or heterocyclyl e.g. furyl or pyridyl group.

X is hydrogen or a coupling-off group. While the coupling-off group may include halogen, or groups linked to the rest of the coupler by a nitrogen or oxygen atom, aryloxy and N-heterocycles such as hydantoin, oxazolidinedione, or succinimido groups are conveniently employed with phenoxy being desirable.

B is hydrogen or a substituent group such as one constituting a Lewis base. A Lewis base is any compound substituent bearing a lone pair of electrons for sharing such as an alkoxy group, e.g. isopropoxy, or a halogen, e.g. chloro.

Z is a substituent group, and n varies from 0–4. These substituent groups, in toto, typically provide a net positive Hammett's sigma para sum when B is an alkoxy or other electron donating group having a negative or neutral Hammett's sigma para value group. Values of the Hammett's sigma para constant may be found, for example, in C. Hansch and A. J. Leo *Substituents for Correlation and Analysis in Chemistry and Biology* Wiley, New York (1979). When B is a halogen, there is less need for a substituent Z, especially one having a positive Hammett's sigma para value sum, from a hue standpoint. Typically, n is 0–2. Substitutions at the 3-, 4-, and/or 5-positions are most useful in many instances. Examples of suitable Z substituents include sulfone, carboxyl, carbamoyl, sulfonamido, sulfamoyl, and cyano groups.
Table I describes dyes and couplers useful in the photographic elements of the invention.
TABLE I
Invention Dye (ID) and Invention Coupler (IC) Examples.
ID-1
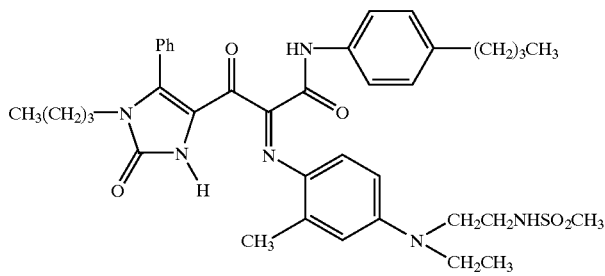
ID-2
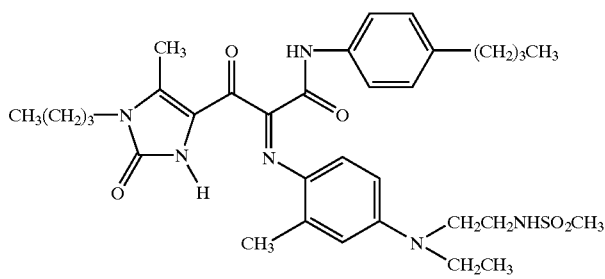
ID-3
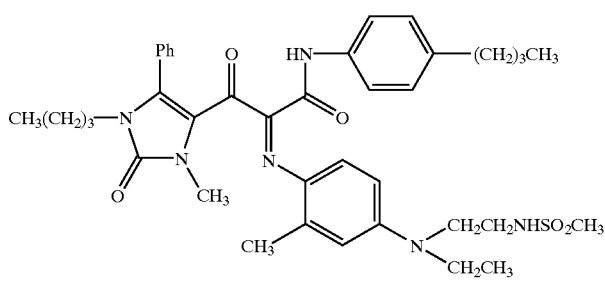
ID-4
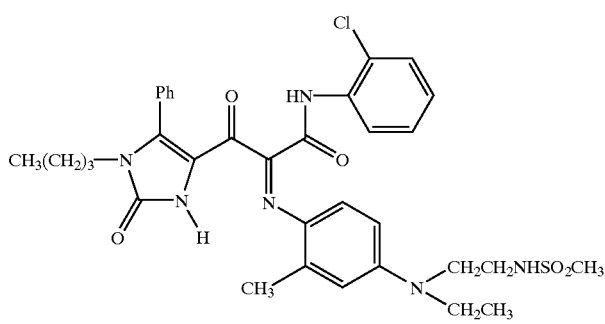
ID-5
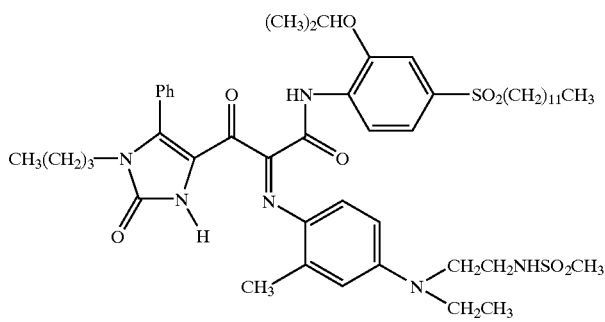

TABLE I-continued
Invention Dye (ID) and Invention Coupler (IC) Examples.
ID-6
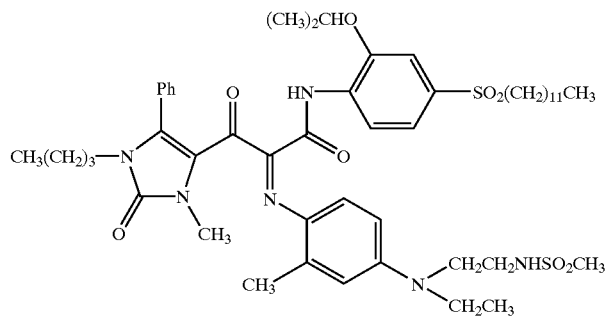
ID-7
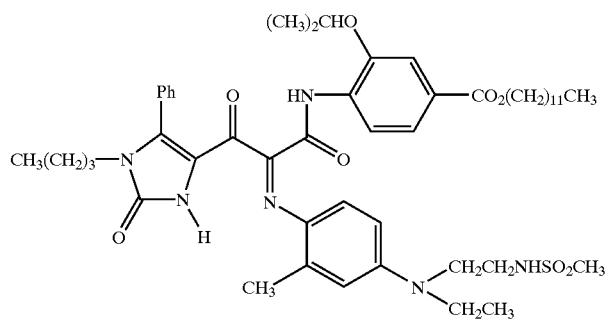
IC-1
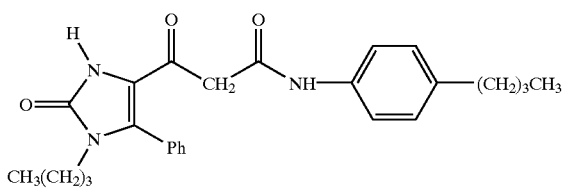
IC-2
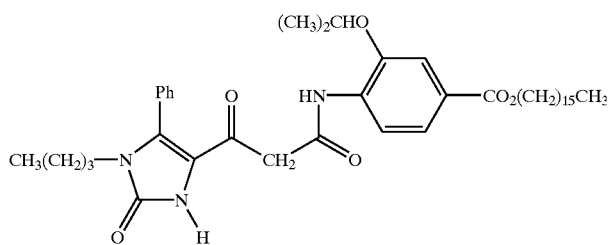
IC-3
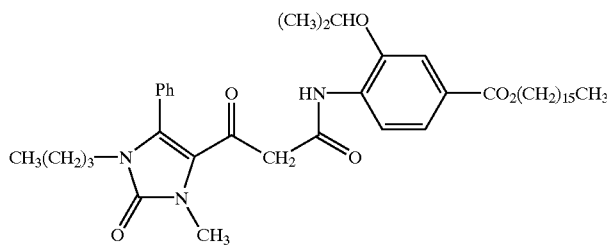

TABLE I-continued
Invention Dye (ID) and Invention Coupler (IC) Examples.
IC-4
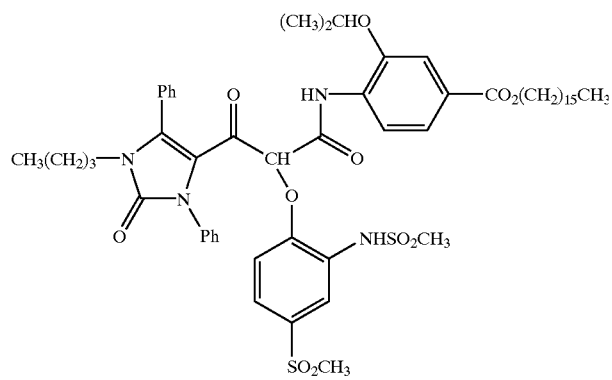
IC-5
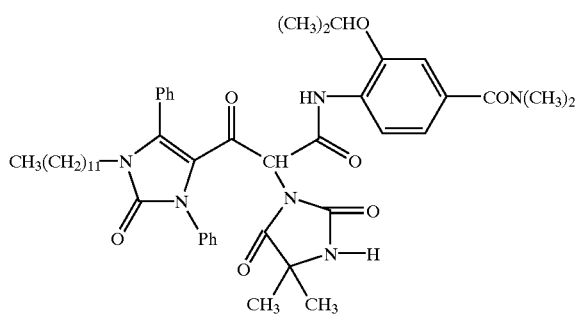
IC-6
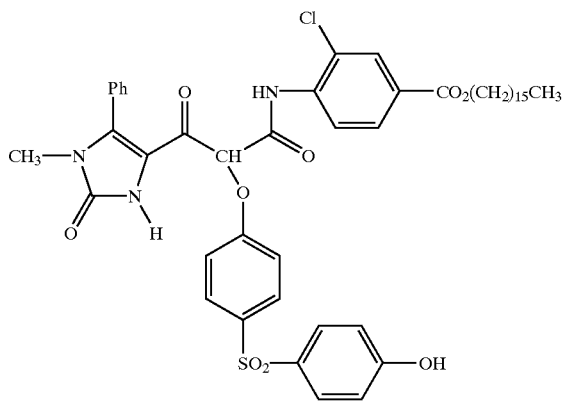
IC-7
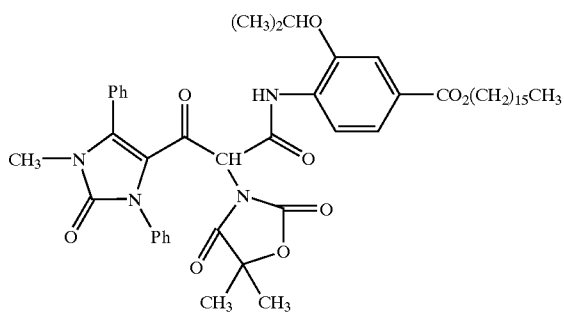

TABLE I-continued
Invention Dye (ID) and Invention Coupler (IC) Examples.
IC-8
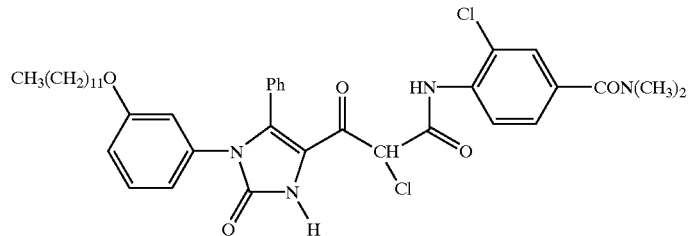
IC-9
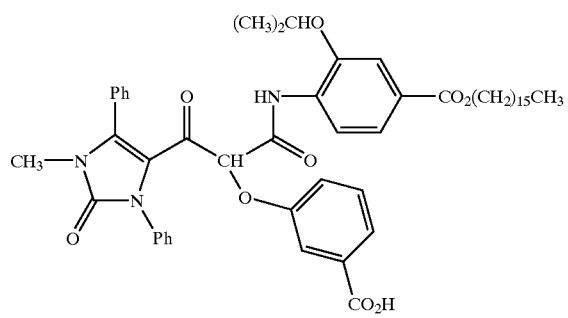
IC-10
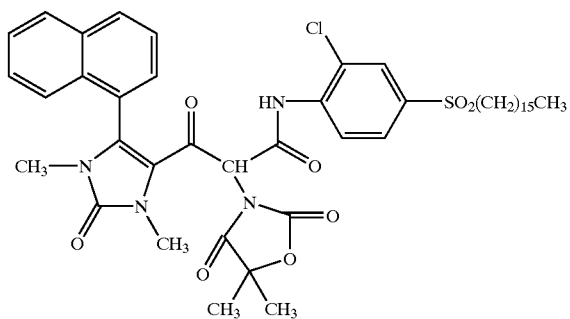
IC-11
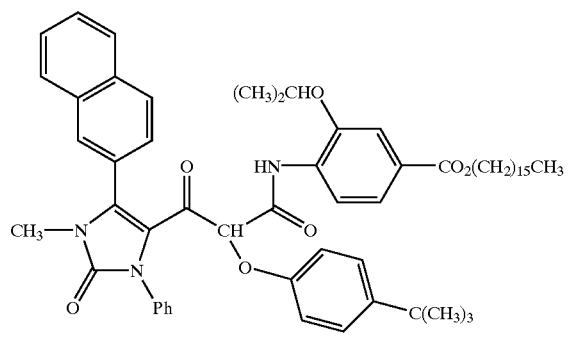

TABLE I-continued
Invention Dye (ID) and Invention Coupler (IC) Examples.
IC-12
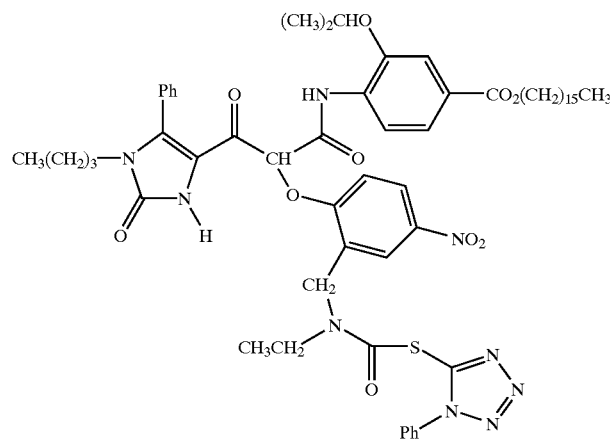
IC-13
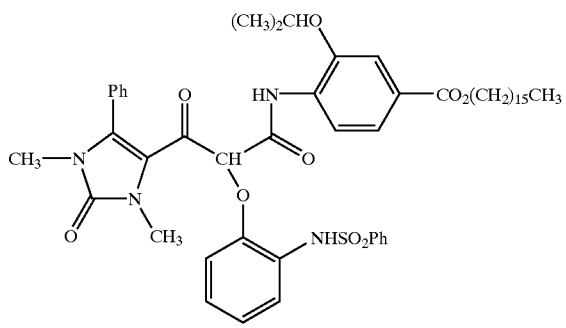
IC-14
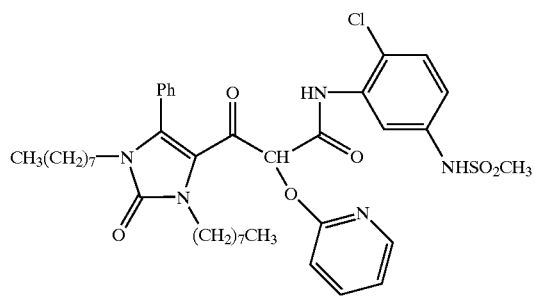
IC-15
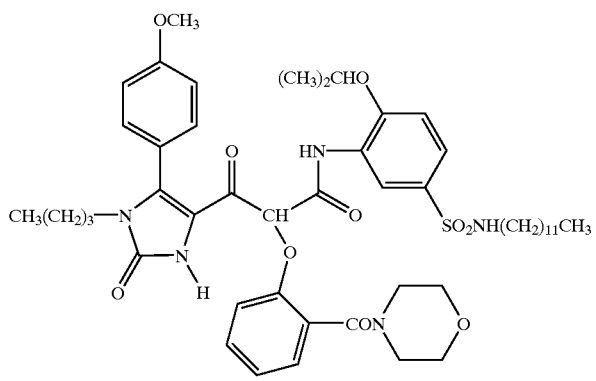

TABLE I-continued
Invention Dye (ID) and Invention Coupler (IC) Examples.
IC-16
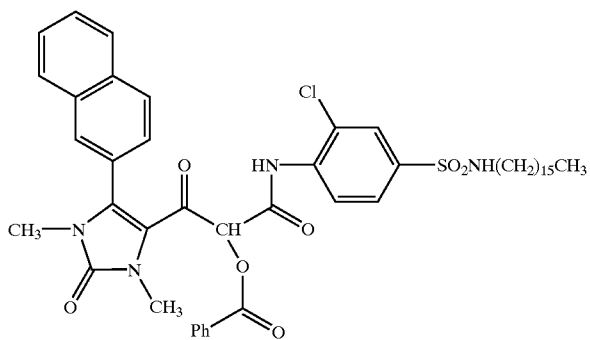
IC-17
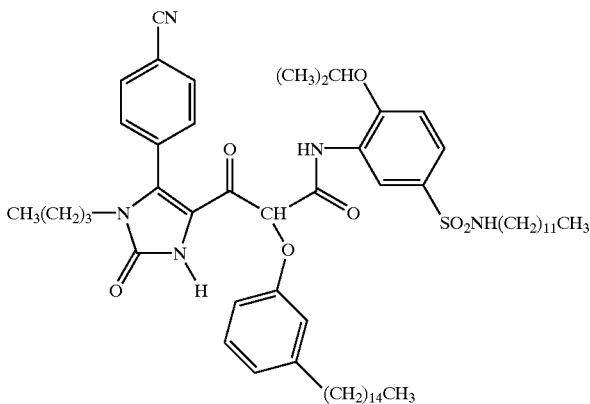
IC-18
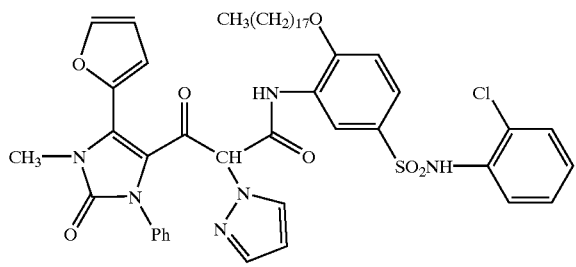
IC-19
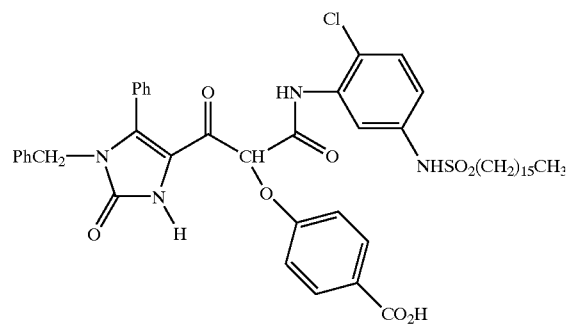

TABLE I-continued
Invention Dye (ID) and Invention Coupler (IC) Examples.
IC-20
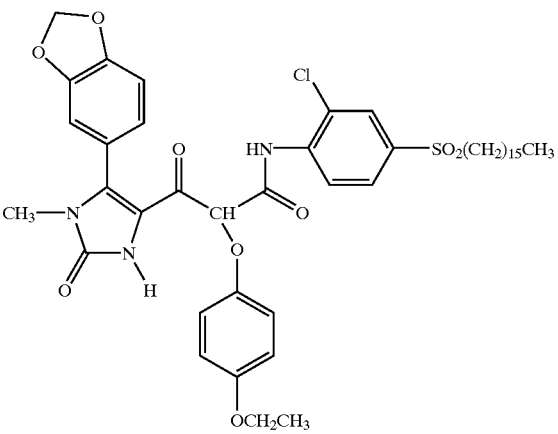
IC-21
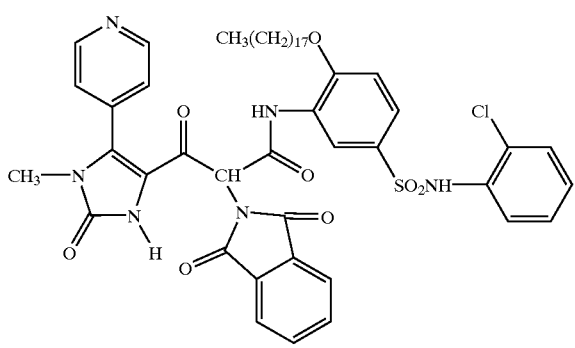
IC-22
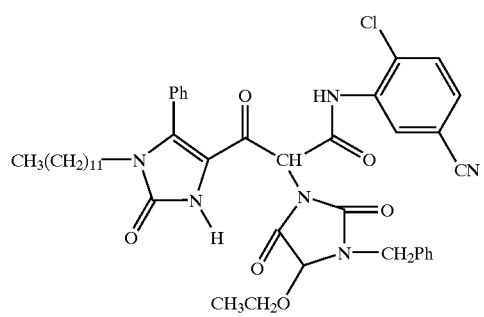
IC-23
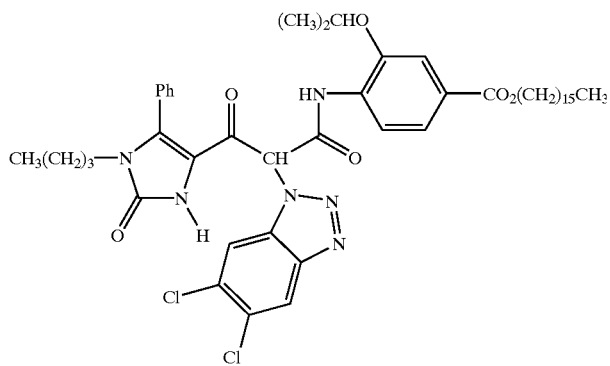

TABLE I-continued

Invention Dye (ID) and Invention Coupler (IC) Examples.

IC-24

[Chemical structure of IC-24]

IC-25

[Chemical structure of IC-25]

IC-26

[Chemical structure of IC-26]

IC-27

[Chemical structure of IC-27]

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-tinmethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethyihexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The materials useful in the invention can be used in any of the ways and in any of the combinations known in the art. Typically, the invention materials are incorporated in a melt and coated as a layer described herein on a support to form part of a photographic element. When the term "associated" is employed, it signifies that a reactive compound is in or adjacent to a specified layer where, during processing, it is capable of reacting with other components.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, and subbing layers.

If desired, the photographic element can be used in conjunction with an applied magnetic layer as described in Research Disclosure, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office. When it is desired to employ the inventive materials in a small format film, *Research Disclosure*, June 1994, Item 36230, provides suitable embodiments.

In the following discussion of suitable materials for use in the emulsions and elements of this invention, reference will be made to Research Disclosure, September 1996, Item 38957, available as described above, which is referred to herein by the term "Research Disclosure". The Sections hereinafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 Research Disclosure, Item No. 36544 referenced above, is updated in the September 1996 Research Disclosure, Item No. 38957. Certain desirable photographic elements and processing steps, including those useful in conjunction with color reflective prints, are described in Research Disclosure, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, and color correction.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455, 169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006, 755A and 2,017,704A.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730, 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783, 5,178,993, 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323; EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877. 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0 422 595; EPO 0 428 899; EPO 0 428 902; EPO 0 459 331; EPO 0 467 327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103, German OLS 3,912, 265; and German OLS 40 08 067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. Nos. 2,298,443; 2,407,210; 2,875,057; 3,048,194, 3,265,506; 3,447,928; 4,022,620; 4,443,536; 4,758,501, 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599, 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654, 5,358,835, 5,358,838; 5,360,713; 5,362,617; 5,382,506; 5,389,504; 5,399,474; 5,405,737; 5,411,848; 5,427,898; EPO 0 327 976; EPO 0 296 793; EPO 0 365 282;

EPO 0 379 309; EPO 0 415 375; EPO 0 437 818; EPO 0 447 969; EPO 0 542 463; EPO 0 568 037; EPO 0 568 196; EPO 0 568 777, EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632, 345; 3,928,041; 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213, 490; Japanese Published Application 58–172,647; U.S. Pat. Nos. 2,983,608; 4,070,191; and 4,273,861; German Applications DE 2,706,117 and DE 2,643,965; UK. Patent 1,530, 272; and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Usually the couplers are dispersed in a high-boiling organic solvent in a weight ratio of solvent to coupler of 0.1 to 10.0 and typically 0.1 to 2.0 although dispersions using no permanent coupler solvent are sometimes employed.

The invention may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477, U.S. Pat. No. 4,163, 669; U.S. Pat. No. 4,865,956; and U.S. Pat. No. 4,923,784, may be useful. Also contemplated is use in association with nucleating agents, development accelerators or their precursors (UK Patent 2,097,140; UK. Patent 2,131,188), electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid, hydrazides; sulfonamidophenols; and non color-forming couplers.

The invention may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the materials useful in the invention may be blocked or coated in protected form as described, for example, in Japanese Application 61/258,249 or U.S. Pat. No. 5,019, 492.

The invention may further be used in combination with image-modifying compounds that release PUGS such as "Developer Inhibitor-Releasing" compounds (DIR's). DIR's useful in conjunction with the invention are known in the ail and examples are described in U.S. Pat. Nos. 3,137, 578; 3,148,022; 3,148,062; 3,227,554; 3,384,657; 3,379, 529; 3,615,506; 3,617,291; 3,620,746; 3,701,783; 3,733, 201; 4,049,455; 4,095,984; 4,126,459; 4,149,886; 4,150, 228; 4,211,562; 4,248,962; 4,259,437; 4,362,878; 4,409, 323; 4,477,563; 4,782,012; 4,962,018; 4,500,634; 4,579, 816; 4,607,004; 4,618,571; 4,678,739; 4,746,600; 4,746, 601; 4,791,049; 4,857,447; 4,865,959; 4,880,342; 4,886, 736; 4,937,179; 4,946,767; 4,948,716; 4,952,485; 4,956, 269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378, 236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969). Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazolnes, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

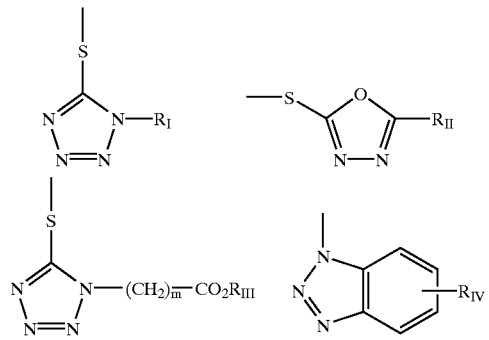

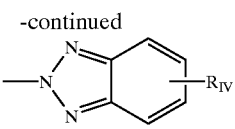

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features describe above. It is typical that the timing group is of one of the formulas:

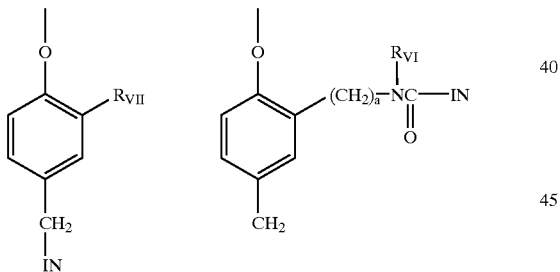

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60–249148 and 60-249149.

Suitable developer inhibitor-releasing couplers for use in the present invention include, but are not limited to, the following:

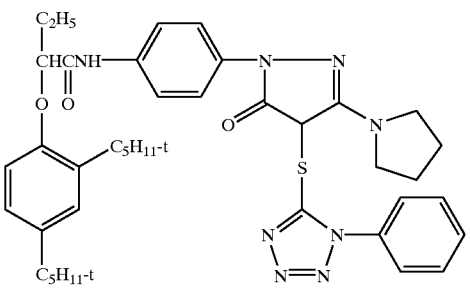

D1

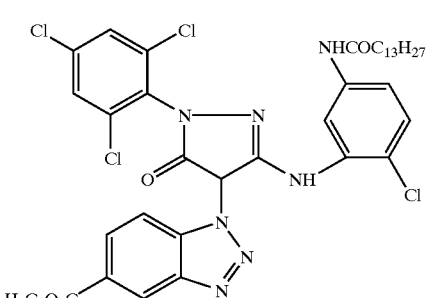

D2

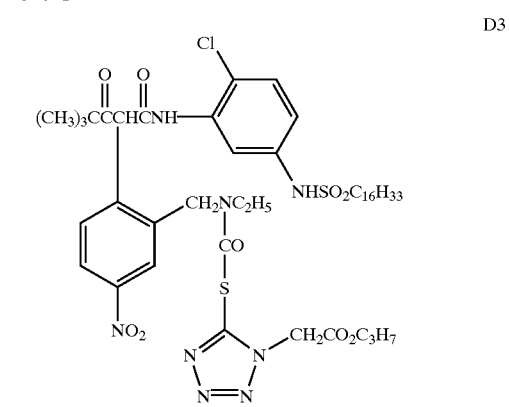

D3

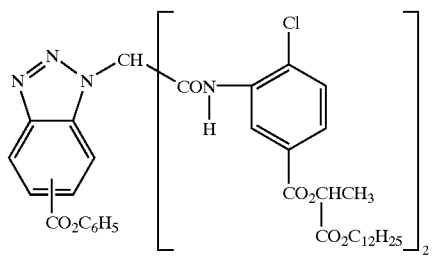

D4

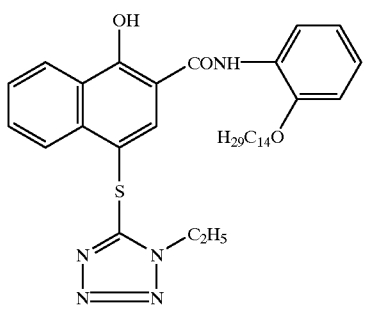

D5

-continued

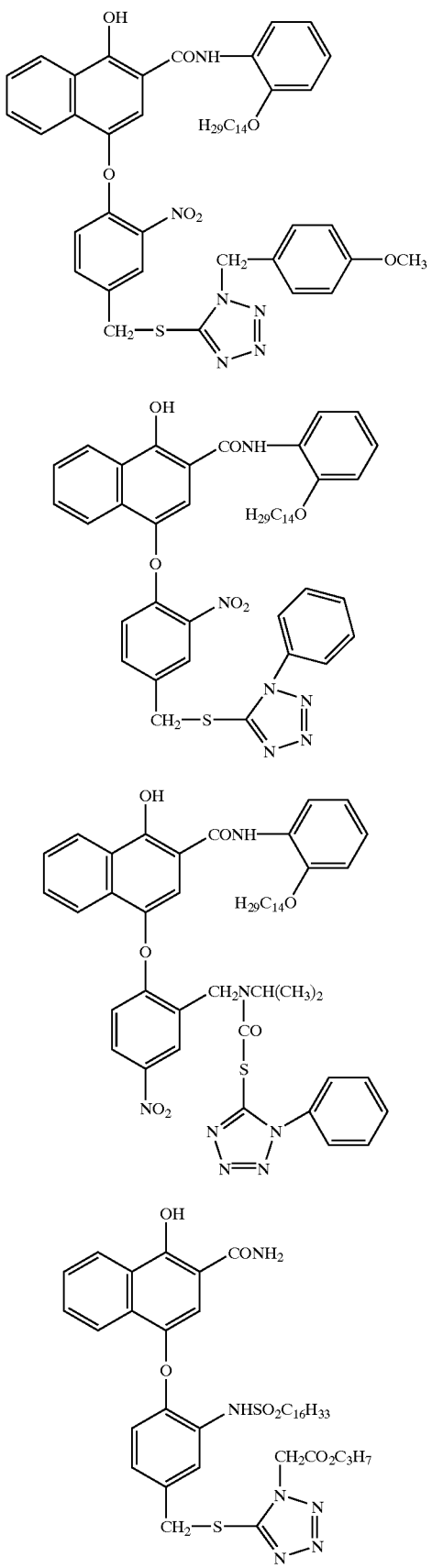

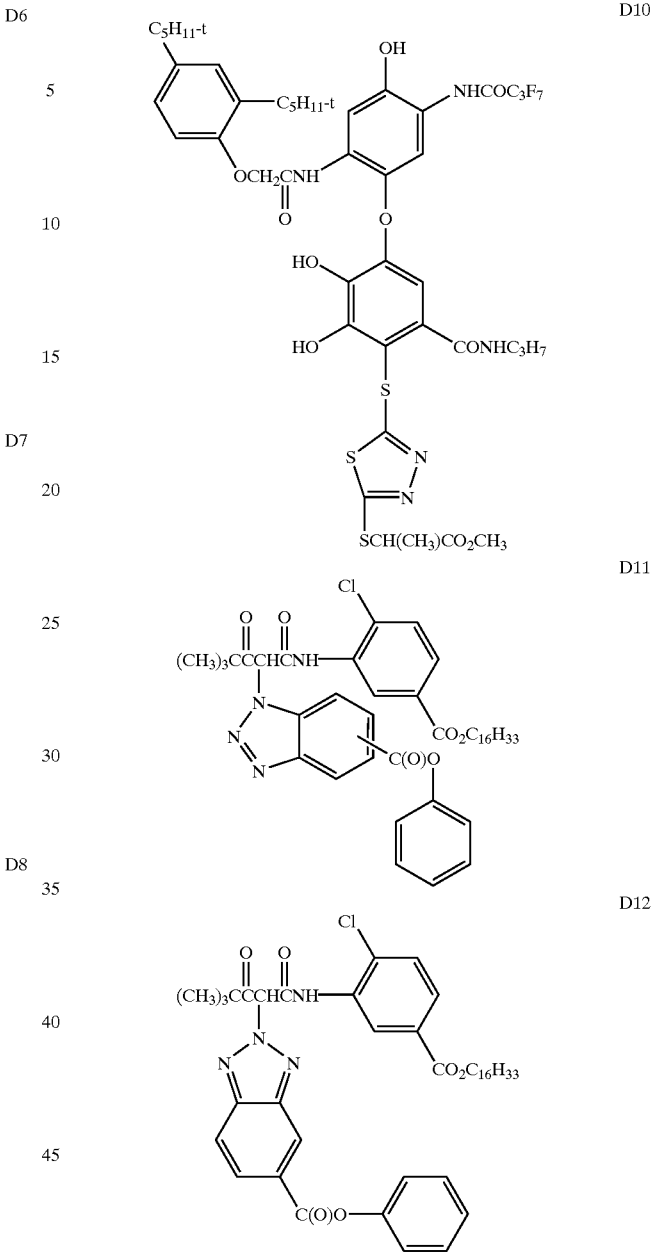

It is also contemplated that the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England. Materials useful in the invention may be coated on pH adjusted support as described in U.S. Pat. No. 4,917,994, on a support with reduced oxygen permeability (EP 553, 339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822, 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669, 90-086,670; 90-087,360; 90-087,361; 90-087,362; 90-087,363; 90-087,364; 90-088,097; 90-093,662; 90-093,663; 90-093,664; 90-093,665; 90-093,666, 90-093,668; 90-094,055; 90-094,056; 90-103,409; 83-62,586; 83-09,959.

Conventional radiation-sensitive silver halide emulsions can be employed in the practice of this invention. Such emulsions are illustrated by *Research Disclosure*, Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of the total grain projected area. Preferred tabular grain emulsions are those in which the average thickness of the tabular grains is less than 0.3 micrometer preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435,501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061,609, Tsaur et al U.S. Pat. Nos. 5,147,771, '772, '773, 5,171,659 and 5,252,453, Black et al U.S. Pat. Nos. 5,219,720 and 10 5,334,495, Delton U.S. Pat. Nos. 5,310,644, 5,372,927 and 5,460,934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713,323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271,858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320,938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color-developing agent to reduce developable silver halide and oxidize the color-developing agent. Oxidized color developing agent in turn reacts with the coupler to yield a dye. If desired "Redox Amplification" as described in Research Disclosure XVIIIB(5) may be used.

A "color negative element" utilizes negative-working silver halide and provides a negative image upon processing. A first type of such element is a capture element, which is a color negative film that is designed for capturing an image in negative form rather than for viewing an image. A second type of such an element is a direct-view element that is designed, at least in part, for providing a positive image viewable by humans.

In the capture element, speed (the sensitivity of the element to low light conditions) is usually critical to obtaining sufficient image in such elements. Such elements are typically silver bromoiodide emulsions coated on a transparent support and are sold packaged with instructions to process in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3' 15" or less and desirably 90 or even 60 seconds or less.

A direct-view photographic element is one which yields a color image that is designed for human viewing (1) by reflected light, such as a photographic paper print, (2) by transmitted light, such as a display transparency, or (3) by projection, such as a color slide or a motion picture print. These direct-view elements may be exposed and processed in a variety of ways. For example, paper prints, display transparencies, and motion picture prints are typically produced by digitally printing or by optically printing an image from a color negative onto the direct-viewing element and processing though an appropriate negative-working photographic process to give a positive color image. The element may be sold packaged with instructions for digital printing or for processing using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less. Color slides may be produced in a similar manner but are more typically produced by exposing the film directly in a camera and processing through a reversal color process or a direct positive process to give a positive color image. The foregoing images may also be produced by alternative processes such as digital printing.

Each of these types of photographic elements has its own particular requirements for dye hue, but in general they all require cyan dyes whose absorption bands are less deeply absorbing (that is, shifted away from the red end of the spectrum) than color negative films. This is because dyes in direct-view elements are selected to have the best appearance when viewed by human eyes, whereas the dyes in image capture materials are designed to best match the needs of the printing process.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal elements are typically sold packaged with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

The photographic element of the invention can be incorporated into exposure structures intended for repeated use or exposure structures intended for limited use, variously referred to by names such as "single use cameras", "lens with film", or "photosensitive material package units".

Preferred color developing agents are p-phenylenediamines such as:

4-amino-N,N-diethylaniline hydrochloride,
  4-amino-3-methyl-N,N-diethylaniline hydrochloride,
  4-amino-3-methyl-N-ethyl-N-(2-methanesulfonamidoethyl)aniline sesquisulfate hydrate,
  4-amino-3-methyl-N-ethyl-N-(2-hydroxyethyl)aniline sulfate,
  4-amino-3-(2-methanesulfonamidoethyl)-N,N-diethylaniline hydrochloride, and
  4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The couplers useful in this invention can be prepared from the requisite heterocyclic parents using variations of the methods outlined in Welter and Reynolds U.S. Pat. No. 6,057,087 and U.S. Pat. No. 6,083,677. Alternatively, such couplers and their related azomethine dyes can be synthesized as outlined in the following.

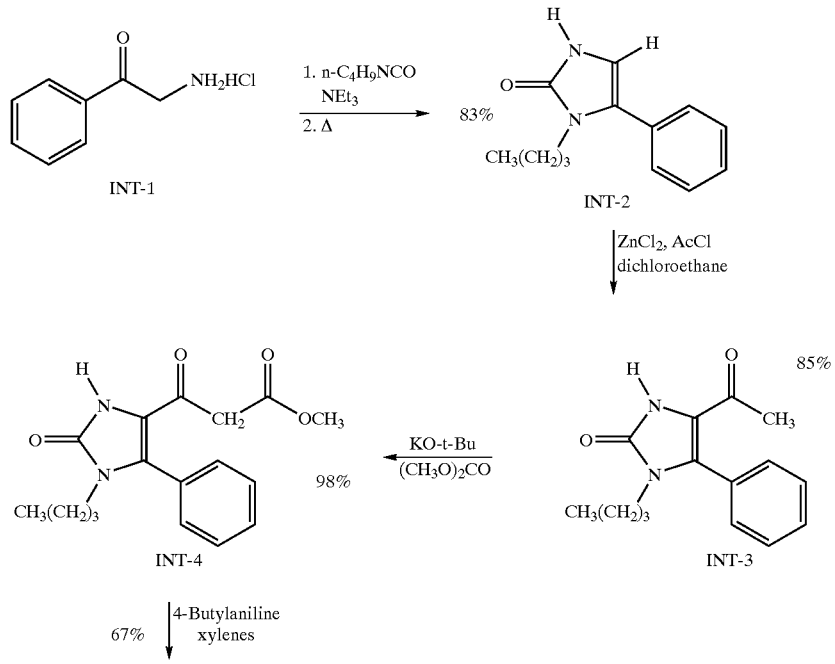

Scheme 1

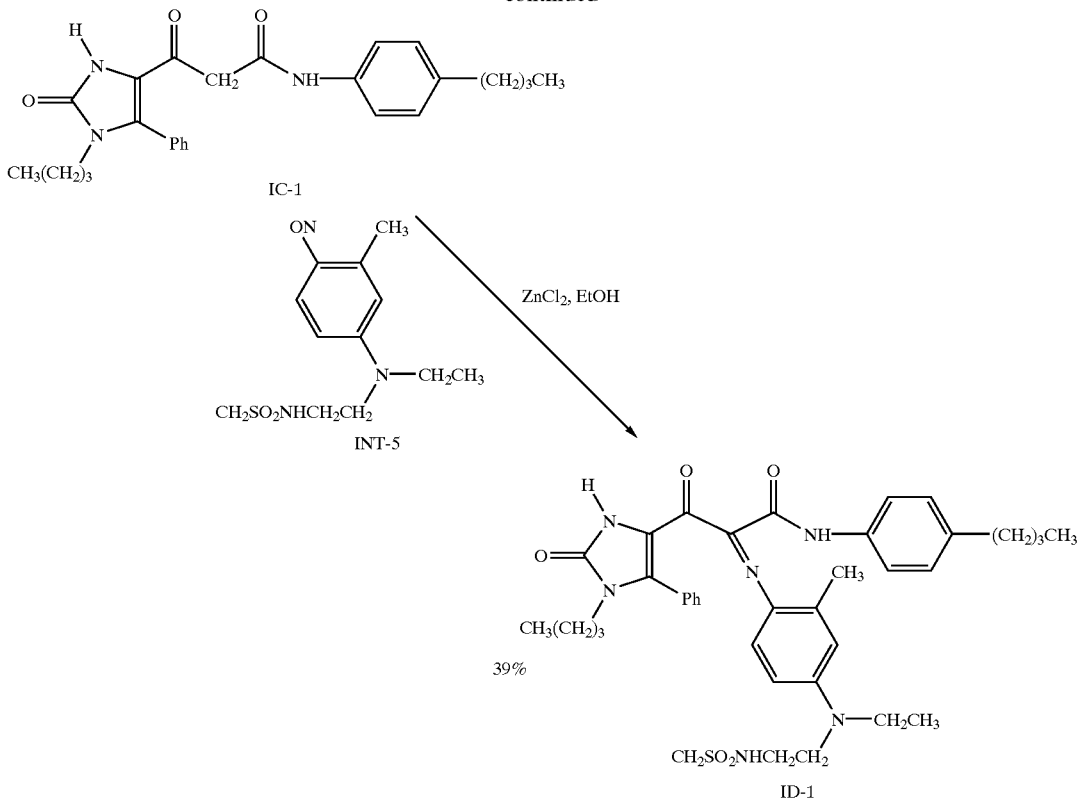

SYNTHETIC PROCEDURES

The following are experimental procedures for the preparation of IC-1 and ID-1 according to the synthetic scheme depicted above (Scheme 1). These procedures may also be extended to the preparation of a variety of other imidazolone couplers.

Preparation of INT-2: A slurry of INT-1 (CAS 5468-37-1; 43.3 g, 0.252 mole) and n-butyl isocyanate (CAS 111-36-4, 25.0 g, 0.252 mole) in 250 mL dichloromethane at ambient temperature was treated dropwise over ten minutes with triethylamine (40 mL, 0.287 mole). The resulting mix was stirred for 0.5 h then washed with dilute hydrochloric acid. The organic layer was dried with sodium sulfate then concentrated in vacuo. The residual oil was heated at reflux in 250 mL toluene for 0.5 h. The solution was concentrated in vacuo to afford INT-2 as a crude oil. This oil was chromatographed on silica gel eluting with mixtures of ethyl acetate in dichloromethane to afford the desired product as a cream solid (34.6 g, 64%), mp 103–104° C. The product proved to be substantially homogenous by thin layer chromatographic (TLC) analysis and displayed spectral characteristics consistent with its assigned structure.

Preparation of INT-3: A mixture of INT-2 (CAS 13870-77-4; 28.1 g, 0.130 mole), acetyl chloride (11.7 g, 0.150 mole), and zinc (II) chloride (17.7 g, 0.130 mole) in 250 mL of 1,2-dichloroethane were heated at reflux for 3 h. The hot mix was poured into ice water. The organics were washed with water, dried with sodium sulfate, and concentrated in vacuo to yield a dark solid. This crude solid was triturated with 150 mL hot isopropyl ether, cooled and chilled. The cold slurry was filtered to provide INT-3 as a tan solid (25.2 g, 75%), mp 132–134° C. The product proved to be substantially homogenous by TLC analysis and displayed spectral characteristics consistent with its assigned structure.

Preparation of INT4: A solution of INT-3 (23.2 g, 0.080 mole) in 350 mL dimethyl carbonate at ambient temperature was treated at once with potassium tert-butoxide (50.0 g, 0.44 mole); a mildly exothermic reaction ensued. The mixture was stirred for 3 h then poured into a mixture of dilute hydrochloric acid and ice. Extractive ethyl acetate workup with sodium sulfate drying provided, upon concentration in vacuo, a dark solid. This crude product was triturated with about 150 mL isopropyl ether to provide INT-4 as a tan solid (25.5 g, 90%), mp 143–144° C. The product proved to be substantially homogenous by TLC analysis and displayed spectral characteristics consistent with its assigned structure.

Preparation of IC-1: A solution of INT-4 (0.32 g, 1.0 mmole) and 4-butylaniline (CAS 104-13-2; 0.3 g, 2 mmole) in 10 mL xylenes was heated at reflux for 0.8 h then stirred at ambient temperature over night. The resulting slurry was filtered. The solid was washed with heptanes and air dried to give IC-1 as a colorless solid (0.29 g, 67%), mp 134–157° C. The product proved to be substantially homogenous by TLC analysis and displayed spectral characteristics consistent with its assigned structure.

Preparation of ID-1: A mixture of IC-1 (0.2 g, 0.51 mmole), INT-5 (CAS 56046-62-9; 0.3 g, 1.1 mmole), and zinc (II) chloride (0.1 g, 0.7 mmole) in 10 mL of ethanol were heated at reflux for 2 h then poured into cold water. Ethyl acetate extractive work up gave a dark oil. Silica gel chromatography, eluting with mixtures of ethyl acetate, tetrahydrofuran and acetonitrile afforded crude dye. Trituration with 1:1 (v/v) propyl acetate/heptanes afforded ID-1 as a yellow solid (0.14 g, 39%), mp 157–158° C. The product proved to be homogenous by TLC analysis and displayed spectral characteristics consistent with its assigned structure.

Table II provides the formulas for the comparative dyes and couplers tested hereinafter.

TABLE II

Comparative Dye (CD) and Comparative Coupler (CC) Examples.

CD-1
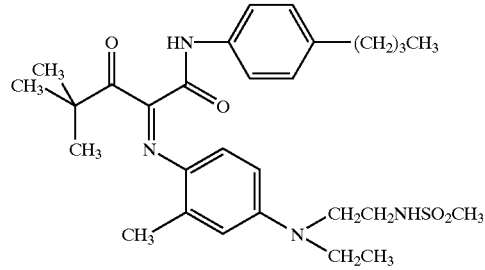

CD-2
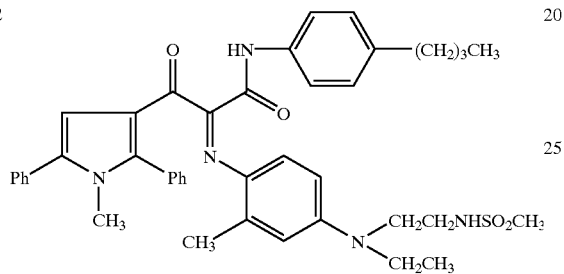

CD-3
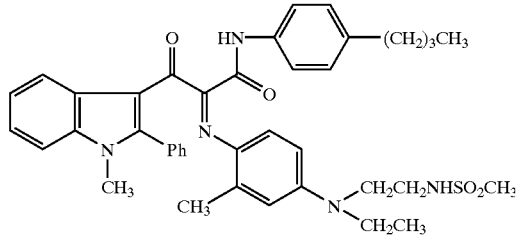

CD-4
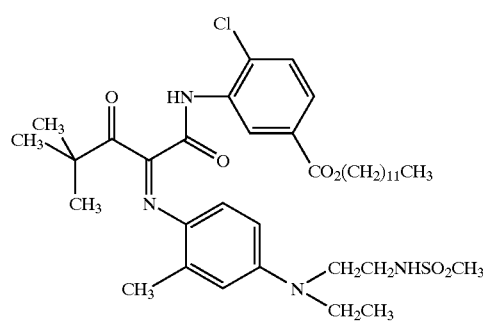

CD-5
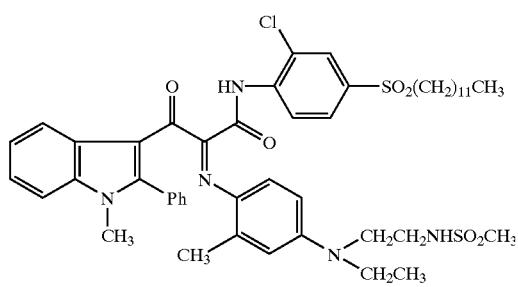

TABLE II-continued

Comparative Dye (CD) and Comparative Coupler (CC) Examples.

CD-6
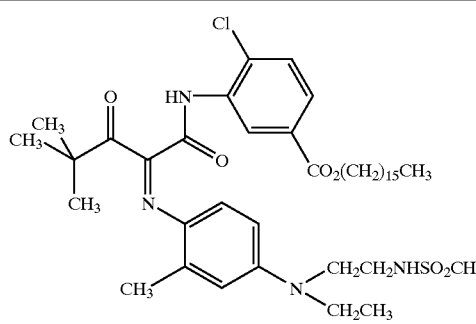

CD-7
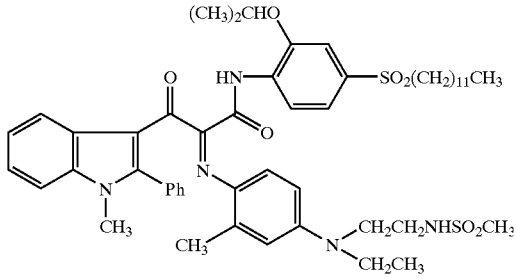

CC-1
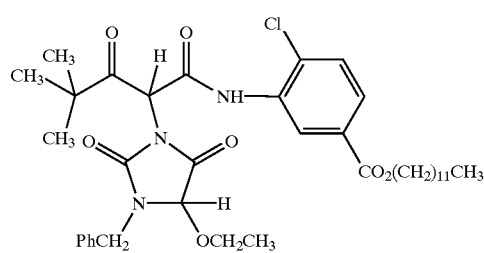

CC-2
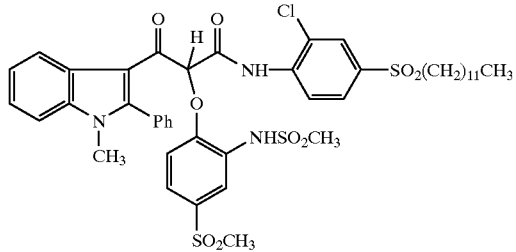

Experimental Results

A. Dye Hues: As mentioned previously, many characteristics of a photographic image depend upon the spectral response of the dyes forming that image. The greater the molar extinction ($\epsilon$-max) of an image-forming dye the less silver and coupler are needed to produce the same dye density, lower silver laydowns often lead to sharper photographic images. The color of a dye depends upon the position of its maximum light absorption ($\lambda$-max). The $\lambda$-max of the dye must be carefully positioned to afford excellent color reproduction; generally a yellow dye $\lambda$-max between 440–450 nm proves most effective. For acylacetanilide couplers, the $\lambda$-max is commonly adjusted via changes in the anilide's substituents. The deeper the intrinsic hue of the parent dye's absorption with a particular anilide structure (e.g., 4-butylanilide), the more readily the desired $\lambda$-max is obtained. Finally, the ideal yellow dye absorbs only light in the blue portion of the visible spectrum; yellow dyes that absorb substantial amounts of green light appear desaturated and therefore yield poorer color reproduction. The bathochromic one-half bandwidth (B1/2BW) is a measure of the degree of unwanted absorption of a particular yellow dye. The B1/2BW is the distance on the dye's spectral response curve, in nanometers, from the λ-max to the wavelength of ½ the maximum absorption on the long wavelength side of the curve. The smaller the B1/2BW distance, the more sharp-cutting is the spectral response of a dye and the better the color reproduction available from the dye. The spectrophotometric response data for several dyes are summarized in Table III.

TABLE III

Dye Characteristics[a]

| Compound | λ-max (nm) | ε-max | B1/2BW (nm) |
|---|---|---|---|
| CD-1 | 428 | 11800 | 42 |
| CD-2 | 426 | 16400 | 36 |
| CD-3 | 426 | 19700 | 32 |
| CD-4 | 440 | 16100 | 39 |
| CD-5 | 446 | 27000 | 32 |
| ID-1 | 435 | 20900 | 35 |
| ID-2 | 436 | 14300 | 42 |
| ID-3 | 432 | not determined[b] | 36 |
| ID-4 | 442 | 21000 | 34 |
| ID-5 | 447 | 24100 | 34 |
| ID-6 | 446 | 21700 | 34 |
| ID-7 | 446 | 21600 | 34 |

[a]Spectrophotometric data derived from dilute acetonitrile solutions of chromatographically homogenous dyes; see Table I for invention dye structures.
[b]Trace impurity precluded accurate measurement of molar absorptivity.

The 4-butylanilide dyes of the invention (ID-1, ID-2, and ID-3) are seen to have a longer λ-max than that of the comparison dyes bearing the same anilide functionality (CD-1, CD-2, and CD-3). The extinction and B1/2BW of these 4-butylanilide, invention dyes are superior to that of the well-known commercial pivaloylacetanilide type dye, CD-1.

B. Photographic Light Stability

Monochrome Photographic Coatings of Several Couplers Were Prepared:

On a gel-subbed, acetate support were coated the following layers:

First Layer: A photosensitive layer containing (per square meter) 3.23 g gelatin, 0.86 g blue-sensitized silver bromoiodide emulsion, a coupler dispersion containing 2.69× $10^{-3}$ mole of coupler, 0.027 g surfactant Olin 10G, 0.055 g surfactant Triton X-200®. The coupler dispersion contained the coupler, coupler solvent (coupler: solvent 1:0.33 di-n-butyl sebacate), 6% gelatin, and Alkanol XC at a level equal to 10% of the weight of the gelatin in the dispersion.

Second Layer: A protective layer containing (per square meter) 0.97 g gelatin and 0.086 g bis-(vinylsulfonyl) methane.

The samples were subjected to stepwise light exposure using the following exposure conditions: IB sensitometer, 0.01 sec using HA-50, DLVa and 0.6 inconel filters, and 0–3 step tablet. Samples were then processed using process E-6 solutions and conditions as follows:

| Process Step | Time (min.) | Temp (C) | Agitation |
|---|---|---|---|
| 1st developer | 3.0 | 36.9 | N₂ burst (2" on, 8" off) |
| 1st wash | 2.0 | 36.9 | |
| Reversal Bath | 2.0 | 36.9 | |
| Color Developer | 6.0 | 36.9 | N₂ burst |
| Prebleach | 2.0 | 36.9 | |
| Bleach | 6.0 | 36.9 | Continuous air |
| Fixer | 4.0 | 36.9 | N₂ burst |
| Final Wash | 4.0 | 36.9 | No Agitation |

Processed film samples are subjected to 5.4 klux, simulated daylight. Density readings were taken at intervals of 0 and 3 weeks: the change density from the exposure at which the original (time zero) strip equals 1.0, and the change blue minimum density (D-min) are recorded in the Table III.

TABLE IV

Three Week 5.4 klux Light Fade Experiments.

| Coated Coupler | Δ Density from 1.0 | Δ Density D-min |
|---|---|---|
| A. First Experiment | | |
| CC-2 | −0.39 | +0.16 |
| IC-2 | −0.17 | +0.03 |
| CC-1 | −0.09 | +0.00 |
| B. Second Experiment | | |
| CC-2 | −0.45 | +0.14 |
| IC-3 | −0.19 | −0.02 |
| CC-1 | −0.09 | −0.01 |

These data clearly indicate that the couplers of the invention (IC-2 and IC-3) afford yellow dyes with light stability superior to the dyes of structurally similar coupler (CC-2). Further, these new couplers afford lower levels of photolytically induced D-min yellowing as compared to the alternative improved coupler technology (CC-2). On the other hand, the new dyes were found to be less light-fast than the commercial pivaloyl dyes (as derived from CC-1) that suffer from low extinction and comparatively poor dye hue (as shown in Table III) or poor hydrolytic stability (as shown in Table V).

C. Hydrolytic Stability: The acid catalyzed decomposition of yellow azomethine dyes has recently been shown to be an important pathway in the degradation of photographic images. Thus, the stability of yellow dyes toward acidic hydrolysis may well be predictive of their stability in color photographic images.

The rates of hydrolysis of a variety of dyes have now been measured using an accelerated solution test format. Solutions of the dyes (6% Triton X-100®) in 0.10 N hydrochloric acid were held at 50° C. The rates of dye destruction were monitored using standard HPLC procedures monitoring at 450 nm. Under these conditions, the dyes exhibited first-order fade kinetics, and the rate constants and associated half-lives are reported in Table V. These data clearly show that the dyes derived from the couplers of this invention (CD-5 and CD-6), afford much greater hydrolytic stability than that provided by the comparison dyes. In particular, the dyes of the invention are much more stable than the commercial pivaloyl dye CD-6. These new dyes are even more resistant to acid catalyzed hydrolysis than the improved 3-indoloyl couplers CD-5 and CD-7.

TABLE V

Kinetics of Yellow Dye Hydrolysis[a].

| Compound | $k_{obs}$ ($m^{-1}$) | $k_{rel}$ | $t_{1/2}$ (h) |
|---|---|---|---|
| CD-5 | $5.38 \times 10^{-4}$ | 3.8 | 21.5 |
| CD-6 | $6.42 \times 10^{-3}$ | 45.9 | 1.8 |
| CD-7 | $2.03 \times 10^{-3}$ | 14.5 | 5.7 |
| ID-5 | $4.13 \times 10^{-4}$ | 3.0 | 28.0 |
| ID-6 | $1.42 \times 10^{-4}$ | 1.0 | 81.6 |

[a]dye in 6% Triton X-100 ® surfactant solution in 0.10N hydrochloric acid at 50° C.

In concert, these data relating to dye hue, light-fastness and hydrolytic stability, clearly establish the couplers useful in this invention to be photographically useful, in fact, superior in many respects to the established structurally similar coupler classes.

The entire contents of the patents and other publications referred to in this specification and in the identified Research Disclosure publications are incorporated herein by reference.

What is claimed is:

1. A photographic element comprising a light sensitive silver halide emulsion layer having associated therewith a coupler represented by formula F-1,

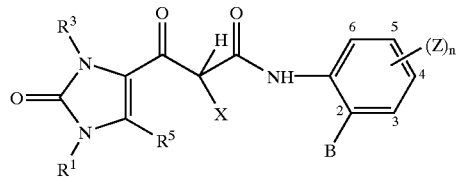

F-1 wherein:

$R^1$, $R^3$ and $R^5$ are independently selected from hydrogen or a substituent group and two of them may join to form a ring;

X is hydrogen or a coupling-off group,

B is hydrogen or a substituent group;

Z is a substituent group, and n varies from 0–4.

2. The element of claim 1 wherein $R^1$ represents a substituent group linked to the coupler by a carbon atom.

3. The element of claim 2 wherein $R^1$ and $R^5$ represent (cyclo)alkyl, aryl, or heterocyclic groups.

4. The element of claim 1 wherein B is a substituent constituting a Lewis base.

5. The element of claim 4 wherein B is a halogen substituent or an aryloxy or alkoxy group.

6. The element of claim 5 wherein B is a chloro substituent.

7. The element of claim 6 wherein B is an alkoxy group.

8. The element of claim 1 wherein $R^1$ is an alkyl group.

9. The element of claim 1 wherein X is hydrogen, a phenoxy group or a nitrogen linked heterocycle group.

10. The element of claim 9 wherein X is a phenoxy group.

11. The element of claim 1 wherein $R^5$ is an aryl group.

12. The element of claim 11 wherein $R^5$ is a phenyl group.

13. The element of claim 12 wherein B is an alkoxy group and $R^5$ is a phenyl group.

14. The element of claim 12 wherein the anilide ring is substituted with a Z substituent having a positive Hammett's sigma para value.

* * * * *